US012747420B1

(12) United States Patent
Chandrasekaran et al.

(10) Patent No.: US 12,747,420 B1
(45) Date of Patent: Sep. 29, 2026

(54) ON-DEMAND ASSEMBLEABLE HETEROGENEOUS CELL-CULTURE PLATFORM

(71) Applicant: North Carolina Agricultural and Technical State University, Greensboro, NC (US)

(72) Inventors: Arvind Chandrasekaran, Greensboro, NC (US); Vikram Surendran, Morrisville, NC (US)

(73) Assignee: North Carolina Agricultural and Technical State University, Greensboro, NC (US)

( * ) Notice: Subject to any disclaimer, the term of this patent is extended or adjusted under 35 U.S.C. 154(b) by 910 days.

(21) Appl. No.: 18/164,534

(22) Filed: Feb. 3, 2023

Related U.S. Application Data

(60) Provisional application No. 63/306,128, filed on Feb. 3, 2022.

(51) Int. Cl.
*C12M 3/06* (2006.01)
*C12M 1/42* (2006.01)
*C12M 3/00* (2006.01)

(52) U.S. Cl.
CPC ............ *C12M 23/16* (2013.01); *C12M 21/08* (2013.01); *C12M 35/06* (2013.01)

(58) Field of Classification Search
CPC ....... C12M 23/16; C12M 21/08; C12M 35/06
USPC ....................................................... 435/283.1
See application file for complete search history.

(56) References Cited

U.S. PATENT DOCUMENTS 10,464,064 B1 * 11/2019 Wikswo ................ C12M 23/34
2014/0322784 A1 * 10/2014 Souza .................... C12N 13/00
435/173.1

OTHER PUBLICATIONS

Chandrasekaran et al. (2017) "Temporal gradients limit the accumulation of neutrophils toward sources of chemoattractant," Microsystems & Nanoengineering, vol. 3(1), pp. 1-8.
Ma et al. (2018) "Bioprinting of 3D tissues/organs combined with microfluidics," RSC Advances, vol. 8(39), pp. 21712-21727.

* cited by examiner

*Primary Examiner* — Michael L Hobbs
*Assistant Examiner* — Lenora A Abel
(74) *Attorney, Agent, or Firm* — Jenkins, Taylor & Hunt, P.A.

(57) ABSTRACT

The presently disclosed subject matter relates generally to precisely integrating spatially-defined three-dimensional cell aggregates with complimentary cell-cultures within a co-culture system. In particular it relates to holding cell aggregates a defined distance from complimentary cell-cultures.

20 Claims, 1 Drawing Sheet

ON-DEMAND ASSEMBLEABLE HETEROGENEOUS CELL-CULTURE PLATFORM

RELATED APPLICATIONS

This application claims priority to and the benefit of U.S. Provisional Patent Application Ser. No. 63/306,128, filed Feb. 3, 2022, the disclosure of which is incorporated herein by reference in its entirety.

TECHNICAL FIELD

The presently disclosed subject matter relates generally to precisely integrating spatially-defined three-dimensional cell aggregates with complimentary cell-cultures within a co-culture system, including a microfluidic system. In particular it relates to holding cell aggregates a defined distance from complimentary cell-cultures.

BACKGROUND

Tumor invasion into the surrounding stroma is a critical step in the process of metastasis, and it is necessary to clearly identify the role of the different microenvironmental factors involved in the regulation of tumor invasion. The Tumor-Immune Microenvironment ("TIME") refers to the different subpopulations of the immune system and their interactions within a tumor microenvironmental niche that have a unique influence on the tumor initiation, development and response to therapies. Neutrophils constitute a significant portion of the immune cells present within a TIME, and their high numbers have, in general, been associated with poor prognosis and drug resistance in patients. Conversely, chemotherapy induced neutropenia has also predicted improved survival rates among cancer patients, thereby raising important questions on the impact of neutrophils in tumor development. In the context of tumor metastasis, research has produced conflicting data in explaining whether neutrophils could promote the metastatic cascade, or support immune reactions inhibiting tumor growth. A fuller understanding of the multifaceted neutrophil functionalities in tumorigenesis is still evolving, but there is a steadily growing appreciation that neutrophils can provide critical insights that are essential to tailor suitable anti-tumor and immunotherapeutic strategies, complementary to current therapeutic approaches.

The Tumor-Vascular Microenvironment (TVME) is a basic functional unit of a tumor etiology. During cancer progression, the aggressive growth of tumor and the resultant metabolic demands result in an overexpression of pro-angiogenic factors including the Vascular Endothelial Growth Factor (VEGF) leading to aberrant vascular microdynamics and the disorganization of normal vasculature into an immature, proliferative, and permeable phenotype, commonly referred to as the tumor-vasculature. The abnormality of tumor-vasculature results in the formation of a complex bunch of branched vascular networks surrounding the tumor, which is not only implicated in the sustenance and development of a tumor but is also associated with the impediment of drug delivery to the Tumor Microenvironment (TME). Thus, protecting the barrier integrity of the vasculature is a useful strategy to subdue the potency of the tumor cells. Recent developments of several novel anti-tumor therapeutic strategies have been aimed towards efficient targeting of the tumor-vasculature.

Due to these pathophysiological functionalities of the tumor-vasculature, it is important that laboratory-based in vitro tumor models incorporate early-stage vasculature as their critical subcomponent, and model their subsequent tumor-induced dysfunctional transformation, which could not only reveal potential therapeutic targets but could nevertheless serve as a more physiologically relevant representation of the overall tumor progression. However, bioengineering of tumor-vasculature is challenging, since it necessitates the integration of multiple tissues, including intact vascular conduits, and their placement in a dynamic and biochemically relevant tumor-specific microenvironment without affecting the principal functionalities of each of the ensembles.

Pro-angiogenic behavior of the tumor-vasculature has traditionally been studied in vitro by modeling the typical tumor-mediated response of the vascular endothelial cells, viz., morphogenic reorganization, invasion, proliferation, and vessel stabilization. Aided by advancements in tissue engineering and microengineering technologies, much of the recent research on tumor-vasculature bioengineering has focused on the synthesis of three-dimensional (3D) tumoroid models grown within synthetic extracellular matrix, and the integration vascular networks with these tumoroids, giving rise to the development of miniaturized co-culture platforms referred to as Tumor-Vasculature-on-Chips ("TVoC"). The integration of microfluidics into such models supports the feasibility of spatial organization and compartmentalization of different cells or tissues to mimic functional vascular networks and establishes relevant biochemical perfusibility between the vascular endothelial cells and the tumor cells for the evaluation of angiogenesis and cell migrations in TVMEs. TVoC are touted as better representuing in vivo tumor behavior, and could be used as cost-effective drug-screening platforms in translational research and other applications such as the maintenance of tissue from biopsies and gene expression analysis.

In addition to the challenges of engineering a perfusable, three-dimensional co-culture platform for long-term cultures, TVoC models often require increased complexity of biofabrication given the high degree of heterogeneity in its organization. Given that the dynamics of tumor-vasculature is largely driven by paracrine interactions, a physiologically relevant TVoC shouldt be capable of maintaining the individual cultures of each cell type, and later upon maturation, co-culturing them on the same platform without establishing direct physical contact to initiate the co-culture. Commercially available inserts in multiwell plate formats, such as for example Transwell®, are capable of maintaining such a co-culture with controlled cell-cell contacts, enabling post-processing of each cell population individually. However, such commerically available systems in general lack design customizability and for 3D tumor cultures, additional effort to carefully prepare the tumoroids within ECM constructs and seed them to the bottom of the well plates or onto the membranes rendering the process incompatible with automated handling. Microfluidic TVoCs have heavily relied upon Poly Dimethyl Siloxane (PDMS) based soft lithography as one of the go-to approaches for biofabrication. But, given that most PDMS based devices with enclosed channels are irreversibly bonded for leak-proof sealing, non-destructive retrieval of the cells or tissue samples from the different microcompartments remains a challenge for closer post-assay functional read-outs. This, in part, limits high-resolution probing of the cell or tissue components used in such devices. Soft-lithography based microfabrication processes involve the use of expensive cleanrooms for initial mold fabrication, which are not readily accessible to non-technical personnel. These drawbacks emphasize the need for innovative bioengineering to design and develop more user-friendly, easy-to-prototype, and mass-producible TVoC models that could still retain compatibility with existing imaging systems and analytical tools, and allow for reliable usage by a broad spectrum of research experts.

Thus, there is a need to engineer a biomimetic Tumor-Immune Microenvironment platform, enabling, for example, identification of prospective neutrophil-based targets that could mediate tumor invasion.

The ability of neutrophils to generate Neutrophil Extracellular Traps (NETs) in response to infectious stimuli is of general interest. Through a sequence of processes collectively termed as NETosis, activated neutrophils release NETs, comprising of decondensed chromatin, histones and DNA, into their surrounding Extracellular Matrix (ECM), forming three-dimensional protein web structures with associated cytotoxic enzymes. While NETs can serve as a host defense mechanism to sequester circulating tumor cells, NETs have been directly associated with the initiation and induction of tumor invasion, aiding metastasis.

In a classical tumor metastasis model, the tumor disseminates as single cells from the primary site by invading into the Extracellular Matrix (ECM), and enters the bloodstream as circulating tumor cells before colonizing onto distant tissues and organs. However, a collective tumor migration mechanism has been observed, wherein tumors invade the ECM as cohesive clusters following a traction established within a tumor microenvironment. The collectively migrating tumor clusters have been detected even in the early stage of cancers and are said to have greater invasive capacity and higher resistance to the therapeutic treatments than the individually migrating tumor cells. Limited information is available about the interactions between the NETs and aggregated tumor clusters that could explain the possible downstream modalities of metastatic aggression of collectively invading tumors. Within a dynamic TIME, neutrophils respond to the tumor-derived chemotactic stimuli by extravasating from the blood vessels into the tumor tissue through chemotaxis and migrate towards the growing tumor aggregates within the stroma, releasing NETs along the way. Without being bound by theory, the collective invasion dynamics of tumors c at least in part depend on the neutrophil influx into the TIME and the consequent NETosis.

There is also a need for an easy to fabricate, magnetically hybrid-integrated Tumor-Vasculature-on-Transwell® (M-TVOT) platform to model tumor-induced pro-angiogenic endothelial behavior, which can be used, for example in rapid drug testing.

SUMMARY

The present application is generally directed to a heterogeneous co-culture system, wherein said system: accommodates cell cultures growing in 2 dimensions and cell cultures growing in 3 dimensions, provides spatial compartmentalization and controllable positioning of 2D cell cultures and 3D tissue and tumor cultures; and integrates the cell cultures growing in 2 dimensions and the cell cultures growing in 3 dimensions in a reversibly attachable manner.

An objective of the presently disclosed subject matter having been stated hereinabove, and which is achieved in whole or in part by the presently disclosed subject matter, other objectives will become evident as the description proceeds when taken in connection with the accompanying drawings as best described herein below.

DETAILED DESCRIPTION

It will be understood that the drawings provided herein are for the purpose of describing embodiments of the inventions and are not intended to limit the inventions thereto.

This description is not intended to be a detailed catalogue of all the ways in which the present invention may be implemented or of all the features that may be added to the present invention. For example, features illustrated with respect to one embodiment may be incorporated into other embodiments, and features illustrated with respect to a particular embodiment may be deleted from that embodiment. Thus, one or more of the method steps included in a particular method described herein may, in other embodiments, be omitted and/or performed independently. In addition, numerous variations and additions to the embodiments suggested herein, which do not depart from the instant invention, will be apparent to those skilled in the art in light of the instant disclosure. Hence, the following description is intended to illustrate some particular embodiments of the invention, and not to exhaustively specify all permutations, combinations and variations thereof. It should therefore be appreciated that the present invention is not limited to the particular embodiments set forth herein. Rather, these particular embodiments are provided so that this disclosure will more clearly convey the full scope of the invention to those skilled in the art.

The terminology used herein is for the purpose of describing particular embodiments of the present invention only and is not intended to limit the present invention. Although the following terms are believed to be well understood by one of skill in the art, the following definitions are set forth to facilitate understanding of the presently disclosed subject matter.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. References to techniques employed herein are intended to refer to the techniques as commonly understood in the art, including variations on those techniques or substitutions of equivalent techniques that would be apparent to one of skill in the art.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or."

As used herein "another" can mean at least a second or more.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

Figure 1A:
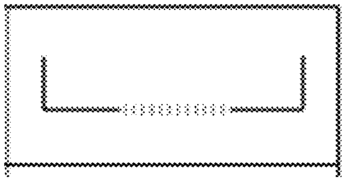
FIG. 1A is a schematic representation of a porous membrane component of one device of the present application.
Figure 1B:
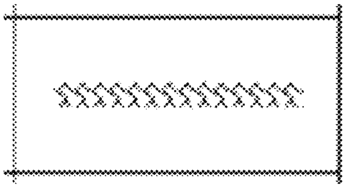
FIG. 1B is a schematic representation of a tissue engineered construct component of one device of the present application.
Figure 1C:
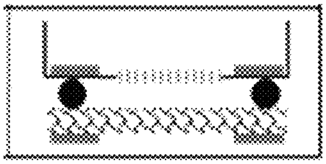
FIG. 1C is a schematic representation of one device of the present application comprising the incorporation of the porous membrane and the tissue engineered construct using a pair of inert, axially magnetized rings, held a fixed distance apart by an O-ring or custom-made washer of defined thickness.

Conventional two-dimensional (2D) culture platforms cannot replicate certain functionalities of a TIME that are specific to three-dimensionality, such as neutrophil infiltration into a 3D tumor cluster, or the collective 3D invasion behavior of the tumor cells. Therefore, disclosed herein is a microfluidics integrated Tumor-Immune Microenvironment-on-Chip (TIME-on-Chip) device that serves as a neutrophil migration and 3D tumor invasion platform. As shown in FIGS. 1A-1C, herein, active tumor spheroid aggregates (henceforth addressed to as spheroids) generated within hydrogel microwells and embedded within collagen matrix with a precise spatial arrangement, are hybrid-integrated with 3D bioprinting-enabled microfluidic channels that are fabricated on a porous membrane and carrying neutrophils. This device design mimics the physiology of a typical TIME in a 3D setting wherein, neutrophils from the microfluidic channel can migrate towards the tumor through the collagen matrix, leading to NETosis and 3D tumor invasion into the stroma. Using representative ovarian cancer cells OVCAR-3, the TIME-on-Chip device demonstrated the collective 3D invasion behavior of aggregated cancer spheroids. The neutrophil response to these tumor spheroids through chemotaxis and NETosis was examined via the impact of neutrophil recruitment on tumor invasion. As shown herein, NET formation induced collective invasion of OVCAR-3 cells into the collagen, and this behavior was reversed by drug-induced abrogation of the NETs. The NETs formed around the spheroids in the stromal extracellular collagen matrix and not the tumor-contacted NETs, predominantly mediate the collective tumor invasion behavior. Tissue-level NETs-stromal interactions can be a potential target for cancer therapeutics.

As shown herein, endothelial culture within microfluidic channels fabricated on a porous membrane, mimicking an intact vascular tubule upon maturation, was magnetically hybrid integrated with tumor spheroids embedded within a collagen matrix, to create a co-culture system representing the Tumor-Vascular Microenvironment with precise spatial positioning of the individual cultures. Using the device, the pro-angiogenic behavior of endothelial cells upon co-culture within a tumor microenvironment to induce angiogenesis was demonstrated, giving rise to an immature, proliferative, and permeable vasculature.

Cellular microenvironments play a critical role in directing cell responses but are typically ignored in conventional in-vitro assay platforms, wherein cells are cultured on hard, flat, plastic dishes that do not represent their in-vivo sustenance conditions. Three-dimensional (3D) culture systems direct cell behavior in distinct, in-vivo-like patterns compared to their two-dimensional (2D) counterparts, however, culturing cells in 3D presents challenges, including a substantial increase in cost of materials for cell culture, greatly increased imaging and analysis time, as well as difficulties in ensuring the control of the passage of soluble factors across the cellular junctions through para-cellular and trans-cellular pathways, analogous to in vivo mass transport through vascular networks. These gaps widen further in cultures involving more than one cell type where it is important to study and delineate the phenotypical changes experienced by the individual cell types in response to the biochemical and mechanobiological signals from within their microenvironment. Added to this complexity are requirements implementing clustered cell aggregates as spheroids or organoid cultures with defined spatial positioning.

Microfluidics integrated Organ-on-a-Chip technology has touted for a wide range of applications, particularly in drug discovery for early identification and screening therapeutics, but critical challenges remain (such as manufacturing and operational complexities, and incompatibility with automated high-throughput analysis). Most Organ-on-Chip platforms with enclosed microfluidic channels are irreversibly bonded to render them leak-proof. But this means non-destructive retrieval of the cells or tissue samples from the different micro-compartments of such systems, and simultaneous maintenance of compatibility with existing analysis and imaging systems for closer post-assay operations can be extremely challenging.

An in-vitro heterogeneous co-culture platform preferentially holds individual cell cultures (such as, for example, spheroid tumor cells and endothelial cells) physically isolated from one another and allows them to develop into their matured phenotypes in their comfortable 3D microenvironments; thereafter the spheroids are integrated as a co-culture with an endothelial cell layer. In this way subsequent regulations in the cellular behavior are driven by their interactions with one another, which is a more realistic representation of many disease models.

One solution for on-demand attach/detach-able cell culture platforms is technology a) simple enough to allow for operational simplicity and assay repeatability, (b) compatible with the currently available high-throughput screening and imaging techniques, and (c) at the same time, sufficiently realistic to improve the translational potential and the ultimate utility of any assay.

As disclosed herein is an on-demand attach/detach-able heterogeneous cellular co-culture platform, a schematic representation of the cross-section is shown in FIGS. 1A-1C and FIG. 2. This system consists of a porous membrane (including but not limited to Transwell insert, a hydrogel membrane or a similar porous surface) to which cells cultured within tissue engineered constructs or similar platform can be readily attached using a pair of inert, axially-magnetized rings. The spacing between the porous surface, and the engineered tissues can be precisely controlled by using a wide array of standard O-rings or custom-made washers of required thickness. The magnetic attachment is self-centering/self-aligning, and can be adjusted as needed throughout the culture process.

Figure 2:
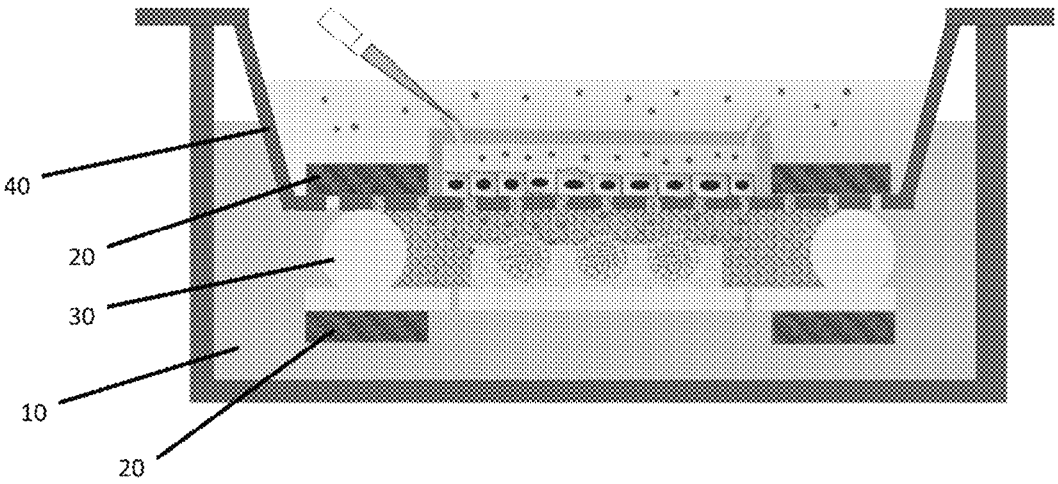
FIG. 2 a schematic cross-sectional image of a hybrid co-culture comprising endothelial cells on a porous membrane comprising insert 40, integrated with spatially defined tumor clusters, comprising a pair of inert, axially magnetized rings, 20, held a fixed distance apart by 30, an O-ring or custom-made washer of defined thickness.

An in-vitro tumor model schematically shown in FIG. 2 was constructed. An endothelial monolayer (HUVEC-Human Umbilicial Vein Endothelial Cells) was cultured on top of a Transwell insert for 48 hours, and spheroids of ovarian cancer cell line (OVCAR-3) were cultured in hydrogel micropockets and embedded within a collagen matrix (creating a 3D tissue with precisely positioned tumor clusters) was hybrid integrated with the endothelial culture using a magnetic assembly of the present application, enabling the endothelial cells to form tight junctions against the tumor spheroid, mimicking an in-vivo tumor. Many 3D in-vitro tumor models involving spheroids are static systems without defined vasculature networks, and the co-culture vascular models showing tight junction formation do not incorporate 3D spheroids but instead incorporate cell monolayers in a 2D culture.

The formation of endothelial tight junctions in the presence of 3D tumor spheroids was observed in the co-culture as described below.

The devices disclosed herein enable one or more of: a) Rapid, on-demand attachment and detachment of the cell-culture ensembles; b) 2D and 3D cell culture on the same system; c) high-throughput scalable integration of multiple porous cell culture substrates into the system; d) integration of multiple 3D cultures with precise spatial distribution (eg: spheroids); e) integration of an unlimited number of layers of cell culture; f) the possibility of rearranging the configuration on-the-fly; g) accommodation of dynamic mechanobiology into the cell culture (for example: integrates the system with fluid flow to simulate stresses induced by blood flow on endothelial cells); h) non-destructive dismantling of the system for post-process analysis of the individual cultures.

In one aspect, the present application discloses a heterogeneous co-culture system, wherein said system: accommodates cell cultures growing in 2 dimensions and cell cultures growing in 3 dimensions; provides spatial compartmentalization and controllable positioning of 2D cell cultures and 3D tissue and tumor cultures; and integrates the cell cultures growing in 2 dimensions and the cell cultures growing in 3 dimensions in a reversibly attachable manner. In one embodiment, the cell cultures are prepared by tissue engineering, using synthetic or clinical tissue samples. In another embodiment, the cell cultures growing in 3 dimensions are spheroids. In another embodiment, the system comprises a pair of inert, axially magnetized rings, optionally held a fixed distance apart, wherein said distance is maintained by an O-ring or washer or similar biologically inert spacer. In one embodiment, the fixed distance is less than about 0.5 mm, or is between about 0.1 mm and about 0.5 mm. In another embodiment, the system further comprises a cell culture platform selected from the group comprising petri dish, multiwell plates, or slides. In yet another embodiment, the system further comprises a first insert comprising a porous substrate, wherein the porous substrate optionally comprises plastic, hydrogel, or biological tissues. In another embodiment, the system further comprises a second insert comprising a porous substrate, wherein the porous substrate optionally comprises plastic, hydrogel, or biological tissues. In one variation of any aspect or embodiment, the cell culture platform is optically transparent or the first and/or second insert is optically transparent. In yet another embodiment, the cell cultures growing in 2 dimensions and cell cultures growing in 3 dimensions are grown independently, optionally to attain fully mature phenotypes, before being integrated into the co-culture system. In yet another embodiment, the system further comprises a cell culture platform comprising a microfluidic system, optionally wherein the cells are co-culture along their apical-basil axis.

An in vivo tumor microenvironment is a highly complex architecture; interactions between tumor cells and their local environment are potential anti-tumor targets. Most available platforms are either non-representative of the complex tumor microenvironment or only suitable for low throughput screening. Reproducing an appropriate in vitro model system of perfused blood vessels and their crosstalk to solid tumors with various environments was a difficult problem solved by the device disclosed herein.

The devices of the present application facilitate imaging the migration of endothelial cells closest to the tumor, which are not possible with simplistic models of tumor-endothelial co-cultures built on planar, two-dimensional culture vessels that may not accurately capture tissue-specific dynamics. Technical limitations persist in known devices, including devices lacking a realistic microenvironment and explant models suffering from a lack of reproducibility and long-term viability. Alternatively, the 3D engineered models disclosed herein revealed important functions of single vessels under normal and pathological conditions.

Many models now mimic in vivo geometries, enabled significantly by the use of microfluidics-based techniques. Along with ease of reproduction, cost-effectiveness and use of flexible polymers such as polydimethyl siloxane (PDMS), microfluidics offers the ability to produce well-defined micron-scale geometries and can be designed to distinguish between subtleties of chemokinetic and chemotactic effects. Combined with biologically derived hydrogels, an increasing number of microfluidic designs have emerged to study 3D lumen and branched networks of capillaries in one of two approaches: predefined patterning or self-assembly.

Engineered in-vitro models of the tumor microenvironment that closely emulate in-vivo tumor behavior of the present application have a wide variety of uses, including but not limited to evaluation of therapeutics and pharmaceuticals. The devices of the present application allow analysis of the individual responses of each subpopulations of cells. Tumor vasculature is a critical component of tumor studies. The pre-metastatic cascade of events involves the dissemination of the tumor aggregates into the stroma and their invasion across a dysfunctional vascular barrier into the bloodstream. Vasculature also provides tumor sustenance and proliferation through supply of oxygen and nutrients. The growth and progression of a tumor is modulated by the highly dynamic stromal interactions with the cancer cells and their combined biochemical cross-talks with the vasculature. The engineering of cellular microenvironments with high degrees of spatiotemporal precision in the device of the present application means that cells can be presented with biochemical signals in a physiologically relevant context, which can limit the size and complexity of vascular scaffold models.

The hybrid integrated 3D systems disclosed herein combine micro-manufacturing technologies and tissue engineering, enabling the fabrication of a tumor-vasculature model capable of mimicking critical physiologic parameters present in vivo, including complex architecture of a tumor microenvironment with multicellular arrangement and extracellular matrix deposition, and a vascular architecture that shows tight junctions, barriers to mass transport of drugs, nutrients and other factors, analogous to in vivo tumor tissues.

The devices of the present application permit customizability the platform to accommodate application-dependent design changes to the different sub-components, such as the microchannel configuration, the organization of the stromal microcompartment and adaptability to most of the standard cell culture dishes.

The overall fabrication procedure of the devices of the present application is rapid, simple, and does not require any specific engineering skill-set.

The disclosed device design provides a robust solution to mimic the physiological tumor microenvironment, for improving predictive accuracy in oncology drug discovery. The device platform enables probing further into the organization of tumor-vasculature and for conducting anti-tumor drug testing targeting the tumor-induced vascular dysfunction.

In one variation, the hybrid-integration process comprises placing a ring magnet aligned with a hollow culture dish containing the microfluidic channel. The spheroid-containing microwell plate is placed on another ring magnet and aligned with respect to pre-made alignment marks. An O-ring is placed on top of the microwell plate and collagen is added inside the O-ring. After gelation of collagen, both the assemblies are brought in proximity to each other for instantaneous magnetic attachment, and creation of the integrated TIME-on-Chip device.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example A

Material and Methods

Unless otherwise mentioned, all materials were procured from Thermofisher Scientific (Carlsbad, CA, USA), and all chemicals from Sigma Aldrich (St. Louis, MO, USA).

A-2.1 Tissue Culture Protocols 2.1.1 Tumor Cell Culture

Chemoresistant ovarian cancer cell line NIH: OVCAR-3 was used as the model tumor cell line. OVCAR-3 cells were cultured in RPMI-1640 Medium (Gibco, USA) supplemented with 20% Fetal Bovine Serum (FBS), 1% Penicillin-Streptomycin and 0.01 mg/ml Bovine Insulin. Culture media was changed every two days. Immediately before the experiments, the cells were detached from the culture plates using Trypsin-EDTA (0.25%), and re-suspended in complete growth medium to the desired concentration. For cell proliferation assays, cells were treated with 5 μM CellTrace CFSE dye (Thermofisher scientific, USA) for 15 minutes, and the media was replaced thereafter prior to trypsinization. OVCAR-3 cell lines used in preliminary imaging assays were modified to express GFP (generously gifted by Dr. Imran Rizvi, UNC Chapel Hill) with an emission peak at 540 nm.

2.1.2 Preparation of Collagen

To prepare collagen matrix, Type-I bovine collagen (Advanced Biomatrix, 5 mg/ml) was diluted to 1.5 mg/ml in PBS, 1x RPMI and 10x MEM solution to obtain the final concentration. The acidic solution was neutralized with 1M $NaHCO_3$ by titration based on the color of the indicator in RPMI. The pre-polymerized collagen was kept in ice until further use. Cold collagen gel solution was pipetted over the test devices and allowed to incubate at 37° C. for 45 min to gel. In some experiments, the collagen was doped with 100 ng/ml of transforming growth factor (TGF)-β or 100 ng/ml of Interleukin-8 (IL-8) to stimulate tumor invasion as required.

2.1.3 Preparation of Polyacrylamide

Polyacrylamide (PAAm) pre-polymer solution is prepared in volumetric compositions of 30% 5.3M Acrylamide stock solution (Bio-Rad), 12% 129.7 mM Bis-acrylamide stock solution (Bio-Rad), 47% of Phosphate Buffered Saline (PBS), and 1% of TetraMethylEthyleneDiamine (TEMED) mixed in an Eppendorf tube. To initiate polymerization, 10% of freshly-prepared 1% w/v Ammonium Persulfate (APS) initiator was added to the solution. The Polyacrylamide formulation had an empirical shear modulus of ~25 kPa.

A-2.2. Design and Fabrication of TIME-On-Chip

The TIME-on-Chip device comprises a composite hydrogel-glass plate having arrayed microwells embossed on the hydrogel surface to house the tumor spheroids; the plate was attached magnetically to microfluidic channels created on a porous track-etched membrane having 3 μm pores. The microfluidic channel replicates an intact vascular structure surrounding the tumor that have a junction gap of ~ 2 μm. A collagen layer filled the space between the spheroids and the channel to mimic the tumor stroma. This configuration allowed in-vivo like 3D biochemical correspondence between the tumor cells, stroma and the vasculature. The device of the present application facilitates the replication of neutrophil infiltration into the tumor tissue across the porous membrane and enables the study of tumor invasion.

2.2.1 Fabrication of Spheroid Microwell Plate

The hybrid hydrogel-glass microwell plate for tumor spheroid generation was fabricated through pattern transfer onto Polyacrylamide (PAAm) by replica molding from negative plastic molds. The microwells had an inside diameter of 500 μm, an opening of 200 μm, with a regular spacing of 600 μm between two adjacent features. The diameter of the Polyacrylamide base was 10 mm consistent with the inner diameter of the ring magnet used for hybrid integration. The microwell molds were 3D printed (Formlabs 3, USA) using standard resin, and PAAm (prepared as described in 2.1.3) was cast on the molds. Surface-treated, silanized glass coverslips were attached with PAAm during polymerization to facilitate handling of the device. After carefully peeling off the PAAm containing embossed microwell features, the devices were immersed in PBS and gently agitated on a shaker plate for 1 hour to remove excess unpolymerized chemicals. Prior to cell seeding, all the devices were stored immersed under PBS at 4° C.

To create spheroids, the plates were firstly sterilized by exposure to germicidal UV light for 30 minutes, and thereafter placed on a flat surface under sterile conditions; the tumor cell suspension (at a concentration of $5\times10^6$/mL) was pipetted onto the polyacrylamide surface. The setup was left undisturbed for 5 minutes to allow the cells to settle into the microwells by gravity. Untreated PAAm resists protein adhesion and so the cells within the non-adhesive microwells spontaneously aggregated to form spheroidal tumor clusters. Thereafter, excess cells on the surface of the microwell plate were gently washed away using culture media. Prior to hybrid integration, the fabricated devices were stored inside multiwell plates under cell culture media for 24 h to allow for the initial spheroid compaction.

2.2.2 3D Bioprinting-Assisted Fabrication of Microchannels

Microfluidic channels were fabricated using a combinatorial technique that involves printing of a sacrificial layer that acts as negative mold, and its subsequent removal upon casting a polymer bulk on top that acts as the enclosure to the channels (see for example, Ma, J., Wang, Y. and Liu, J., 2018. Bioprinting of 3D tissues/organs combined with microfluidics. RSC Advances, 8(39), pp. 21712-21727), leveraging the automated functionality of a 3D Bioprinter (Bio X, CellInk, VA, USA). Commercially available Pluronic gel (IK50000, CellInk, USA) was used as the sacrificial material to print the negative microchannel features, given its ability to gel at room temperatures even at relatively low concentrations, and reverse the gelation to transition into a dissolvable solution upon cooling below its lower critical gelation temperature. UV curable polymer NOA63 (Norland Inc., USA) was used as the channel enclosure. Nucleopore track-etch membrane, 25 mm in diameter with 3 μm pores (Whatman Inc., USA) attached to the bottom of standard 35 mm culture dishes with a central 10 mm bore, was used as the platform for creating the microfluidic channels.

For microchannel fabrication the pluronic layer was printed on top of the membrane precisely along the desired coordinates relative to reference alignment marks. For support, a thin layer of Gelatin-Methacrylate (GelMA-C, IK-351102, CellInk, USA) was printed on top of the pluronic layer. Microfluidic tubes (EW-06419-01, Cole Parmer, USA) were stably positioned over the desired inlet and the outlet locations. NOA63 was then printed on top of the membrane such that it filled up the space surrounding the channel. This step was followed immediately by exposure to 365 nm UV light for 5 minutes for curing the UV sensitive polymer. Printing of NOA and exposure to UV directly on the 3D printer bed helped control the amount of the dispensed NOA, and hence the curing time. This step also reduced manual handling of the device during fabrication.

After UV curing, the setup was then cooled down to 4° C. for 15 minutes using a temperature controlled print-table, and thereafter, the microfluidic tubes were flushed with cold PBS, to remove the sacrificial ink and create a perfusable channel on top of the porous membrane. All the fabricated channels were straight channels having a square cross-section with width and height of 500 μm, and length of 8 mm, unless otherwise specified.

2.2.3 Hybrid Integration and Assembly

The process of hybrid integration of the microfluidic assembly with the spheroids employed Neodymium rare-earth ring magnets (R1090, SupermagnetMan Inc., USA) with inner diameter of 10 mm, outer diameter 22 mm and thickness of 0.4 mm. Firstly, a ring magnet was placed and aligned inside the culture dish (containing the microfluidic channel printed on the porous membrane) concentric with its central bore. The microwell plate, housing the spheroids, was placed atop a counterpart ring magnet and aligned carefully to the reference marks on the magnet. An O-ring with desired thickness is placed on top of this assembly and collagen gel was gently pipetted on top of the microwells to completely fill up the space inside the O-ring. The integration procedure involved bringing the culture dish close to the microwell plate assembly while maintaining it upright to enable attachment of the ring magnets. The ensembles sandwich between the two ring magnets effectively and immediately. The O-ring prevented any fluid leakage from the system while providing the appropriate space (e.g. height) for the stromal collagen layer between the tumor cells and the microfluidic channel. Culture media was then flown into the microfluidic channel (replenished every 12 h) and the devices were incubated at 37° C. till further assays. For neutrophil tumor interaction assays, after culturing the spheroids for 24 h to allow for compaction, neutrophils were loaded into the microchannels, and thereafter quickly hybrid integrated with the spheroids-collagen assembly as disclosed herein.

A-2.3 Neutrophil Isolation and NETs Formation

Neutrophils were isolated using a previously established protocol (Chandrasekaran, A., Ellett, F., Jorgensen, J. and Irimia, D., 2017. Temporal gradients limit the accumulation of neutrophils toward sources of chemoattractant. Microsystems & Nanoengineering, 3(1), pp. 1-8) that generally involves collection of whole blood drawn from the peripheral vein of healthy donors, separation of nucleated cells from the erythrocytes, rinsing the cells, and thereafter magnetically separating the red blood cells from the purified neutrophils. This neutrophil isolation method depletes all other cells from blood, leaving the neutrophils unstimulated. The isolated neutrophils were treated with 16.2 μM Hoechst 33258 dye (H21491, Invitrogen) at 37° C. for 15 minutes for nuclear staining, and prepared to a final concentration of $1\times10^7$/mL for the experiments unless otherwise specified.

Whereas naïve neutrophils were allowed to form NETs by interacting with tumor cells, externally stimulated NETs were generated using 500 nM Phorbol-12-Myristate-13-Acetate (PMA) wherever required. Depending on the assay, PMA was added either to the media containing the suspension of neutrophils prior to passing the cells into the channel, or added directly to the collagen. The generation of NETs from neutrophils was observed by fluorescent labeling using 2.5 UM Sytox Green (S7020, Invitrogen) added to the pre-polymerized collagen (described in 2.1.2.) For experiments that required the inhibition of NET formation, neutrophils were re-suspended in RPMI containing 10 μM Sivelestat (HY-17443, Medchemexpress) prior to use in the experiments.

A-2.4 Immunostaining

For stimulated tumor migration assays, spheroids were labeled for E-cadherin and nuclei in culture, using standard indirect immunostaining techniques. The microwell plates containing the spheroids were initially washed in PBS and fixed in 4% (v/v) paraformaldehyde in PBS for 1 h at room temperature. Thereafter the devices were washed twice with PBS for 5 min each and permeabilized with 0.1% (v/v) Triton-X in PBS for 1 h at room temperature. After washing 2 times with PBS for 5 min each again, the spheroids were blocked against non-specific binding with 2.5% (v/v) goat serum in PBS for 1 h at room temperature. Devices were then incubated overnight at 4° C. with mouse anti-E cadherin monoclonal antibody (HECD-1) (13-1700, Invitrogen) in a 1:200 dilution of goat serum. 200 μl of the antibody solution was dispensed on top of the device and the setup was left undisturbed for 1 hour at room temperature. The devices were washed twice once again with PBS for 10 min each and blocked with 2.5% (v/v) goat serum in PBS for 1 h. After blocking, samples were incubated at room temperature for 2 h with goat anti-mouse IgG (H+L) secondary antibody, Texas Red-X (T-6390, Invitrogen) in a 1:1000 goat serum dilution. The samples were rinsed for 10 min in PBS and counterstained with nuclear DAPI stain (D3571, Invitrogen) (2 μg/ml in PBS) for 1 h at room temperature, and were thereafter washed twice with PBS. For immunofluorescent staining of citrullinated Histone H3, primary antibody Anti-Histone H3 antibody (ab5103, Abcam) was conjugated with AlexaFluor 647 using Zip AlexaFluor 647 Rapid Antibody Labeling Kit (Z11235, Invitrogen), and the conjugated antibody was added (1:1000) to the pre-polymerized collagen.

A-2.5 Imaging and Statistical Analysis

Both brightfield and fluorescent imaging were carried out using an inverted fluorescence microscope coupled with a CCD camera (Olympus IX-83). CellSens image analysis software (Olympus) was used for data acquisition. Image processing and analyses were done using Image-J (NIH, USA). The experimental data of the calculated spheroid parameters (fluorescence intensity or area) or neutrophil parameters (neutrophils count or % NETs) for different experimental conditions are expressed as mean±standard error (SEM) unless otherwise specified. In general, comparative data analysis of populations was performed without pre-specifying a required effect size. Datasets were normally distributed, with similar variances between compared groups. All statistical analysis was conducted using student's t-test or two-tailed one-way ANOVA analyses with Tukey post-hoc pairwise comparisons (Prism; GraphPad Software, La Jolla, CA). p-values less than 0.05 were considered significant.

Typical interactional dynamics between pre-metastatic tumor and neutrophils extravasating across intact vasculature into the tumor tissue, generate Neutrophil Extracellular Traps (NETs), and initiating tumor invasion into the stromal region. Tumor spheroids housed within hydrogel microwells (such as polyacrylamide) were embedded within a collagen matrix, and integrated with a microfluidic channel through a porous membrane. Neutrophils were loaded into the microfluidic channel (mimicking the vasculature) migrate across the porous membrane (mimicking the vascular lining) into the collagen region (mimicking he tumor stroma) towards the spheroids, and the tumor cells invaded three-dimensionally into the ECM.

A-3. Results 3.1 TIME-On-Chip Facilitates Dynamic 3D Tumor Cultures 3D tumor spheroids were consistently generated using the method described herein. Most of the spheroids appeared circular upon formation. The tumor aggregates were confined within the microwells, and subsequent addition of collagen on top, or magnetic attachment to the microfluidic channel, did not distort the spheroids. In general, the magnetically enabled hybrid integration approach provided robustness to maintain the integrated assembly free of distortion from vibrations associated with handling the device (during transfer of culture vessel or repeated movement of the microscope stage for imaging). This method of hybrid integration also enabled on-demand attach/detachment of the setup during both pre- and post-processing steps, and provided maneuverability to precisely align the different subcomponents under the microscope. Different microfluidic channel configurations with controlled positioning with respect to the spheroids along all three coordinate axes, similar to the framework of the vasculature-like networks were fabricated and tested.

To ensure that the magnetic hybrid integration method sustaines consistent fluid and mass transport across the different interfaces, the diffusion behavior of 10 kDa FITC-dextran from a straight microfluidic channel into collagen (thickness 250 μm) and polyacrylamide layers was studied. This diffusion was quantified by measuring the fluorescence intensity across the spheroids located away from the field of view of the microchannel. The experimental diffusion behavior was compared with the 2D Finite Element Model built on COMSOL. The average fluorescence intensity around a chosen spheroid was measured over time, and the rate of change of concentration was measured by calculating the change in the normalized fluorescence intensity over time, and comparing with the change in the normalized concentration variation obtained from the computational model. The results of the FEM showed a close agreement with the experiment within a 3 h timespan. As shown, the magnetic hybrid integration ensures connectivity across the interfaces of the different layers of the system, and demonstrated the capability of the platform to enable three-dimensional interstitial fluid transport around the spheroids to support long-term cultures.

A-3.2 Demonstration of Collective 3D Migration of OVCAR-3

Migrating OVCAR-3 cells can exist as single cells or as multicellular aggregates. A 3D collagen matrix migration assay is one method to analyze the migration of cells within a physiologically similar 3D environment. Without being bound by theory, aggregated OVCAR-3 cells may undergo spontaneous migration when present in a 3D matrix. Spheroid motility upon stimulation with IL-8 and Tumor Growth Factor-Beta (TGF-B) were tested; both have been shown to induce epithelial to mesenchymal transition (EMT) and to promote migration in OVCAR-3 cells. In separate assays, the collagen layer was doped with 100 ng/mL of TGF-β or IL-8 as the respective experimental condition, and observed tumor behavior over 24 hr. To quantify the spheroid behavior, a parameter called spheroid distortion (ϕ), was defined as the ratio of change in the projected area of the migrated spheroids over the initial projected area of the intact spheroids. The spheroid distortion was analyzed in correlation with the down-regulation of E-cadherin, a marker for cell-cell adhesion. For each experimental condition, the device was non-destructively dismantled after the assay to fix the cells with 4% Paraformaldehyde, and stained for E-cadherin and nuclear stain. The mean E-cadherin per spheroid was measured by calculating the ratio of integrated E-cadherin fluorescence per spheroid over the projected spheroid area.

At baseline, OVCAR-3 cells did not display spontaneous migration into the collagen matrix for at least 24 h. A non-significant increase in spheroid distortion was observed in 48 h, with further distortion at 72 h. No significant difference in the mean E-cadherin signal intensity per distorted spheroid was seen at different time points of the spontaneous migration. However, when exposed to the stimulants, TGF-β or IL-8, the resultant distortion of the spheroids was significantly higher ($p<0.001$) than unstimulated spheroids. The mean E-cadherin expression of the spheroids was significantly reduced under stimulated conditions. Upon stimulation, the cells migrated into the collagen matrix, and the final projected area of the distorted spheroids was always larger than the initial spheroid area ($\phi>0$) suggesting that in a 3D setup, OVCAR-3 cells migrated and invaded as a group rather than as single cells. The migratory cells at the periphery did not appear to change their morphology to mesenchymal-like. While it is possible that cells within a 3D matrix could undergo both proliferation and migration, unstimulated OVCAR-3 generally remained largely in a proliferation-quiescent state within a 3D matrix, suggesting that upon stimulation, the OVCAR-3 spheroids collectively invaded the collagen matrix.

As shown herein one device of the present application, TIME-on-Chip, allows one to recreate and analyze the locomotion behavior of 3D tumor cultures, and carry out integrated labeling and post-assay analyses directly.

A-3.3. OVCAR-3 Spheroids Elicit In-Vivo Like Neutrophil Response

To understand how neutrophils interact with OVCAR-3 spheroids, simulated and visualized chemotaxis and NET formation behavior of naive neutrophils in response to the tumor, to recapitulate aspects of in-vivo neutrophil function in an in-vitro setting. Neutrophils were loaded into the microfluidic channel and their surveillance was presented with competing tumor targets, classified as S1, S2, and S3 based on the arrayed location of the spheroids inside the collagen matrix with respect to the channel. To recreate a physiologically-relevant environment, parallel experiments were carried out in which the fluid carrying the neutrophils inside the channel was actuated using an external syringe pump at a flow rate of 2 μL/hr. Neutrophil response to tumor under both no-flow and flow conditions was analyzed over 6 h.

Neutrophils migrated to the spheroids through the collagen matrix. The inception of neutrophil chemotaxis occurred as quickly as 30 minutes after loading of the cells into the channel. A count of the number of neutrophils that migrated shows that under no-flow conditions, neutrophil trafficking stabilized over ~6 h, without being bound by theory this could be the typical ex vivo lifetime of the neutrophils. Under both no-flow and flow conditions, not all the neutrophils in the vicinity migrated towards the spheroids even over a short migration range, and overall, a maximum of ~10% of all neutrophils from the microchannel infiltrated into the tumor, with ~6% influx observed within the stromal collagen layer. However, in the absence of spheroids, no random migration of the neutrophils into the collagen region was observed, confirming that neutrophils respond to the tumor spheroids through chemotaxis. For both no-flow and flow conditions, no significant difference was observed in the respective mean neutrophil penetration into the spheroids regardless of the spheroid location, suggesting that neutrophil infiltration into a tumor was not dependent on their migration range. Under flow conditiions, neutrophils infiltrated significantly deeper ($p<0.0001$ for S1 and S2, and $p<0.05$ for S3) into the spheroids, with a mean penetration of ~10% greater than the neutrophil infiltration under static conditions.

Spheroids closest to the microchannels recruited the maximum number of neutrophils, with the percentage recruitment dropping as the distance between spheroids and the channel increased. With fluid flow in the channel, a greater number of neutrophils were present in the farthest spheroids (S3) than was seen under no-flow conditions. Without being bound by theory, while the ability of the neutrophils to infiltrate a tumor could depend on the resultant degradation of inter-spheroidal cell-cell tight junctions, it is possible that the shear stress caused by the fluid flow could prematurely activate the neutrophils in the channel leading to altered tumor response.

The reciprocal effect of OVCAR-3 spheroids on the infiltrating neutrophils were characterized. Within 1 h, neutrophils extruded webs of DNA that were detected by the Sytox stain, under both flow and no-flow conditions. In general, the Sytox stained features that were observed in the collagen layer surrounding the spheroids were markedly more spread out than those formed inside the tumors. Without being bound by theory, this could be due to the higher mechanical stiffness around a neutrophil when present inside a condensed microenvironment of a spheroid that might restrict the spread of the extracellular mesh sprouting into the surrounding environment. As a positive control, in separate experiments, neutrophils embedded within collagen were doped with 500 nM PMA, a potent inducer of lytic NETosis. The structures of the extruded features from PMA stimulation were similar to those formed by the neutrophils migrating towards the spheroids, suggesting that OVCAR-3 cells induce the neutrophils to NETose. As another control to validate that NETs induction was specific to the neutrophil interaction with tumor cells, the spheroids in the microwells were replaced with Interleukin-8 doped collagen droplets. IL-8 is a known neutrophil chemokine, and while it stimulated neutrophil chemotaxis from the microchannel into the collagen, no spurious NET formation was observed.

The inter-spheroidal NETosis were characterized by the total number of distinct NET structures within the spheroids and the fold increase in the NETs spread area. Irrespective of the proximity of the spheroids to the channel, under flow, a significantly greater ($p<0.05$) number of NETs structures were present in each of the spheroids, albeit with a significantly lower spread area. To examine this further, the non-adherent neutrophils washed away from the channels under flow were collected and observed Sytox signaling in several of those cells, whereas under non-flow conditions, neutrophils that remained in the channel did not show any Sytox signaling. Without being bound by theory, the shear stress from the fluid flow could rupture the cell membrane possibly leading to budding of the NETs, suggesting that fluid flow around the neutrophils activate them differently and affect their response to tumors.

As shown herein, OVCAR-3 spheroids induce neutrophil response through both chemotaxis and NETosis.

A-3.4. NETs Stimulate OVCAR-3 Invasion

At the end of the 6 h neutrophil-tumor interaction assay, some spheroids (under both flow and no-flow conditions) changed shape by losing their initial circularity. While this morphological disturbance could merely be due to the intrusion of additional cells into the spheroids, the spheroids marginally elongated only at certain sites along their periphery. Spheroid circularity was defined as the ratio of the perimeter of a spheroid to the ideal perimeter of a circle of an equivalent projected area. The loss of circularity correlated with the cumulative total number of NETs and intact neutrophil cells present within the spheroids. The counter-effects of neutrophil-tumor interactions on spheroid distortion was examined over an extended duration (24 h). Neutrophils were loaded into microfluidic channels aligned directly over the spheroids with a separation of 250 μm and no flow was introduced in the channel.

OVCAR-3 cells have limited ability to migrate spontaneously in the absence of infiltrating neutrophils in the TIME. In the presence of neutrophil infiltration, however, spheroid distortion was observed in all the spheroids over 24 h. This distortion was more pronounced than the patterns observed following stimulation with TGF-β or IL-8 perhaps because the OVCAR-3 cells appeared to collectively invade the collagen matrix in a highly directional manner. Since NETs formation was a complementary response of the naive neutrophils, separating the action of NETs and non-NETosing neutrophils in inducing tumor migration was evaluated. The neutrophils were pretreated with 10 μM Sivelestat, a Neutrophil Elastase Inhibitor (NEI), to block NETs formation. The number of extensive NET structures clearly diminished due to NEI treatment. While no significant difference was observed in the number of non-NETosed neutrophils that infiltrated the spheroids, the inter-tumoral NETs density significantly reduced ($p<0.0001$) upon treating the neutrophils with Sivelestat. The resultant spheroid distortion also dropped significantly ($p<0.0001$) compared to untreated neutrophil infiltration. Thus, blocking NET formation impeded the neutrophils' ability to stimulate OVCAR-3 invasion into the collagen matrix, suggesting that tumor cell-derived factors that stimulate neutrophil mobilization through chemotaxis do not necessarily also trigger NETosis.

The DNA mesh from the NETs can entrap the tumor cells at the site of their dissemination and migrate along with them, inflamed neutrophils sequestered at entrapped tumor cells via chemotactic confinement could also promote tumor migration, but it is not known if this dynamic applies to cells migrating in clusters, wherein subpopulations of OVCAR-3 cells within the spheroids could acquire phenotypic variations and neutrophils preferentially home to and infiltrate the more motile cells within the tumor aggregate to NETose. The overall NETs distribution was calculated within the distorted spheroids, and the fraction of NETs present within the spheroid domain invading into the collagen was significantly lower than the NETs fraction present within the intact domain of the distorted spheroids. The NETs present in the invasive domain were not seen specifically at the leading edge of the invading cells, suggesting that NETs do not necessarily trap the more motile OVCAR-3 phenotypes and drag them out of their intact domain to initiate the tumor invasion cascade.

The invasive domain was identifiable due to its protrusion into the collagen matrix outside of the microwells and to its directionality, i.e inclination of the spheroids to migrate along a certain direction. To quantify this polarization, the distorted spheroid was considered as an ellipsoid, and the projected boundary fit with an ellipse that approximately passes through its outermost points. The polarization of spheroid distortion (y) was defined as the aspect ratio of the ellipse i.e ratio of the diameters along its major and minor axes. The average NET-induced spheroid polarization was significantly greater than those observed with TGF-β ($p<0.05$) or IL-8 ($p<0.001$). However, in 3D, while the cells invaded the collagen towards the microfluidic channel no infiltration of the tumor cells was observed across the porous membrane even in the presence of NETs.

The OVCAR-3 cells were stained with CellTrace CFSE fluorescent proliferation marker prior to the spheroid formation to confirm that the spheroid distortion was due to tumor invasion and not proliferation. As a negative control, the spheroids were treated with a combination of 0.6 μM Dasatinib and 30 nM Gefitinib (both of which are known to inhibit OVCAR-3 proliferation) and compared the mean fluorescent intensity of the drug-treated spheroids with untreated spheroids and spheroids distorted in the presence of NETs. No significant difference in the mean signal intensity between the spheroids cultured simultaneously under different conditions. The fraction of cells that retained their fluorescent signal in the invasive region of the collagen was analyzed and compared with the cells in a regular 2D culture. The results showed that most of the cells invading into the collagen retained their fluorescence even in the presence of NETs, and this number was significantly greater ($p<0.05$) than the number of cells that expressed CFSE in the 2D culture over the same culture duration.

Thus, NETs play an important role in OVCAR-3 cells acquiring a pro-migratory/invasive phenotype. NETs stimulate the invasion of OVCAR-3 cells into the collagen matrix and inhibiting NET formation abrogates tumor invasion.

A-3.5 Availability of Stromal NETs Positively Correlates with Collective Invasion of OVCAR-3

For aggregated OVCAR-3 cells, given their tendency to migrate collectively, the inter-spheroidal NETs CAN promote invasion by acting to concentrate NET-associated proteases to cleave or interfere with the cell-cell adhesion within the spheroid. The concentration of inter-tumoral neutrophils WAS MEASURED by pipetting them directly onto the spheroids, allowing them to adhere and washing away the unbound cells before adding collagen gel on top. After 24 h, even though a substantial population of these neutrophils produced NETs, the resultant spheroid distortion was negligible. Since Sytox may stain dead tumor cells with compromised membranes, NETs were immunostained with Anti-H3Citrulline, a NETs-specific marker, conjugated with Alexafluor647. While NETs production was identified by both Sytox and citrullinated histone H3 markers, no significant difference was observed in the spread area of the NET-like structures suggesting that the viability of the tumor cells is largely not affected in the presence of NETs.

Tumor cells may pick up NET-based cues available within the TIME either from the stroma or from the channel. In the present system, the involvement of NETs generated from naive neutrophils outside the spheroid is within the collagen. Within a continuous system, it is not possible to create conditions wherein the neutrophils that infiltrate from the microchannel are physically restricted to remain active only within the collagen without migrating all the way to the spheroids, therefore the effect of varying the stromal NET density on the spheroid distortion was studied by testing different loading concentrations of neutrophils in the channel. The percentage of NET structures occupying the collagen layer increased proportionally to the initial number of neutrophils present in the channel. While the elevated neutrophil concentration also increased the number of tumor-infiltrating neutrophils, the non-tumor infiltrating neutrophils that initially migrate into the collagen may undergo NETosis within the stroma; the count was proportional to the initial neutrophil concentration.

Variation in the stromal NET density was tested by altering the height of the collagen layer for a fixed neutrophil concentration in the channel ($1\times10^7$/mL). The maximum neutrophil infiltration occurred when the distance to the spheroids was minimal, beyond a certain minimum thickness of the collagen layer, corroborating with the NETs density within the collagen region. The percentage recruitment dropped with increase in collagen thickness, possibly due to the increased migration distance for the neutrophils from the channel, thereby eliciting lesser chemotactic response. At the highest neutrophil concentration ($1\times10^7$/mL), the maximum NETs density in the collagen region was not greater than 12%. Whenever there was a higher availability of NETs within the stromal collagen region, the resultant spheroid distortion was also greater.

The tumor spheroids response to NETs produced in the microfluidic channel were studied by leveraging the advantage of the magnetic hybrid integration for on-demand attachment and detachment of the ensembles of the present application. Neutrophils were cultured separately in the microfluidic channel, and stimulated for NETs with 500 nM PMA for 6 h. The conditioned media that seeped out of the porous channel was collected and added back to the collagen layer on top of the spheroids and incubated for 1 h, before attaching the channel with the spheroid-collagen assembly. More than 60% of the neutrophils NETosed within the channel upon PMA stimulation. Irrespective of the NET density or the proximity of these NETs to the spheroids, the resultant spheroid distortion observed after 24 h was negligible. No significant difference was observed in the distortion of spheroids due to either direct stimulation with PMA or by stimulation of neutrophils in the channel with PMA, suggesting that stromal NETs, and not the tumor-contacted NETs or the vascular NETs, play a significant role in mediating the collective invasion of OVCAR-3 from an aggregated state.

A-4. Discussion

As shown herein, neutrophils responded to a growing tumor aggregate through two mechanisms, namely chemotaxis and NETosis, and the interaction with neutrophils elicited a complementary response from the tumor cells through migration and invasion into the stroma. When present within a 3D collagen matrix, tumor spheroids formed by the aggregates of OVCAR-3 ovarian cancer cells displayed a conserved migratory behavior that required additional instigation to proliferate. OVCAR-3 cells migrated cumulatively rather than as individual cells disseminating from the original aggregate. In general, the migration of OVCAR-3 was dependent on the down-regulation of E-Cadherin.

Without external NET-inducing agents such as the PMA, tumor-associated inflammatory factors trigger naive neutrophils to produce NETs. Most in-vitro assays stimulate neutrophils with PMA for the production of NETs. However, PMA could also have counter-effects upon direct interaction with tumors, which may lead to spurious results in a co-culture system.

NETs are known to play an active role in tumor metastasis. The availability of NETs at the destination site is also reflective of the metastatic potential of certain tumors. The dynamics of NET induction and the mechanisms by which NETs facilitate tumor metastasis are unclear. The experimental tumor proliferation assays disclosed herein suggest that NETs, formed in the surrounding stroma of a TIME and not the NETs generated by the tumor-infiltrating neutrophils, regulate the collective migration and invasion of cancer cell aggregates. NET-induced collective tumor invasion is specific to the interaction of the NETs with the collagen matrix surrounding the spheroids and the stromal NETs appeared to stimulate the collective invasion of the tumor cells into the tissue, and the expansion of the aggregated cell colonies.

In general, the NETs generated in the stromal collagen region showed a greater spread than the NETs produced within the spheroid. These data do not support a role for NETs even within ‘leaky vasculature’-like microfluidic channels in enhancing the extravasation of the tumor cells into the channel. On the contrary, the OVCAR-3 spheroids displayed negligible distortion when exposed to a rich, PMA-stimulated NETs microenvironment outside the collagen region. The manner of distortion was not distinguishable from the patterns of weak spontaneous migration of the tumor cells within the 3D matrix. The collective invasion of tumor spheroids is specific to the NETs-collagen interactions, and it is not due to the tumor-chemotactic factors or other components ejected out of the neutrophils during NETosis.

Stromal-tumor interactions are highly dependent on the physical properties of the ECM, and the regulation of collective OVCAR-3 migration by the stromal NETs may be mediated through biophysical transduction. Given the nature of the components released during NETosis, the proteins that are typically associated with the NET structures (elastase, cathepsin G, myeloperoxidase, and histones) may interact and bind directly with the collagen and other proteins present within the ECM, to form complex interlinked structures that result in altered properties of the matrix architecture. It is possible that the physical parameters of the collagen matrix such as stiffness, pore size, and fiber reorganization could differ, leading to modified chemical cues, adhesive ligand densities, or the availability of binding sites to integrins and other matrix receptors. Each of these features can impact tumor motility and gene expression. NETs can increase the stiffness of collagen matrix and (1-integrin is known to mediate NETs-tumor interactions. However, not much attention has been paid to the mechanobiological modalities through which the NETs accumulating around a tumor, could influence the stroma and subsequently influence tumor development. While DNAse treatment effectively degrades the NETs and thus limits the complementary effects on tumor progression, research shows that the degradation process leaves behind fragments of NETs which could still be biologically active. Amidst other multifarious dynamics, NETs could regulate the initiation of tumor invasion through mechanotransduction, through biophysical tailoring of the tissues in and around a TIME. Dismantling the mechanical architecture of the NETs with DNAse treatment could reduce tumor invasion.

As shown herein studying tumors on a three-dimensional (3D) platform offers unique insights into tumor behavior compared to 2D cultures. While dimensionality based functional differences can also exist in neutrophil response, conventional laboratory-based cancer models built on planar, two-dimensional culture vessels appear too simplified to faithfully mimic the tissue-specific diversities of neutrophil dynamics, and may not accurately represent the pathophysiology of tumor progression within a TIME. Spheroids are, in general, considered similar to an early vascular stage of tumors. Tissue-engineered 3D tumor models, consisting of spheroids or organoids grown within synthetic extracellular matrix constructs, have enabled more rigorous tissue level studies of the TIME, and restore important architectural and stromal cues.

The TIME-on-Chip model disclosed herein is capable of recreating in-vivo like neutrophil extravasation and NETosis functionalities within a tumor microenvironment, laying the foundation for conducting immune-tumor dynamics studies in three-dimensional relevance. The device easily enabled the biomimicry of certain exclusive NETs-associated functionalities and their reciprocal effects on tumor development, which are otherwise impossible to implement on conventional in-vitro assay platforms. The device enables a rapid, reproducible method to integrate functional 3D spheroids with tissue-engineered perfusable microfluidic channels to mimic the tumor-stromal-vascular organization. The versatility of the device also facilitates rapid incorporation of additional biophysical functionalities of in-vivo relevance (for e.g. interstitial fluidics or hemodynamics) without the need for drastic design modifications. Moreover, the hybrid integration method disclosed herein facilitates easy dismantling and reassembly of all the sub-components for post-processing procedures such as immunostaining and imaging. This hybrid integration with magnetic attachment can be implemented on a variety of macro-culture vessels, including but not limited to, multiwell plates and Transwell inserts.

The TIME-on-Chip device of the present application enables sophisticated recapitulation of certain critical in-vivo biological events in a physiologically-relevant 3D-microenvironment.

Example B

Material and Methods

Unless otherwise mentioned, all materials were procured from Thermofisher Scientific (Carlsbad, CA, USA), and all chemicals from Sigma Aldrich (St. Louis, MO, USA).

2.1 Design and Fabrication of Hybrid-Integrated Tumor-Vasculature-On-Transwell® ("M-TVoT")

The basic architecture of an M-TVOT device of the present application comprised an open microfluidic component with endothelialized channel surface fabricated on a hydrophilic porous membrane attached to a customized 3D printed Transwell® insert; the component was hybrid integrated to a tumor spheroid array generated within hydrogel microwells and embedded within a collagen matrix. The space between the spheroids and the endothelialized channel was filled with collagen which mimics extracellular matrix (ECM) around the tumor cells, and also acts as the vascular basement. Polyacrylamide (PAAm) was used as the hydrogel material for the fabrication of the microwells, and the PAAm microwells were housed on a perforated PDMS disk with monolithically built-in gaskets. The gasket sandwiched the collagen layer between the microwells and the porous membrane, while the perforations on the PDMS disks enabled media transfer to maintain the tumor cell culture.

Trans-Endothelial Electrical Resistance (TEER) measurements to assess endothelial adherent junction integrity used an open channel, confining printing of the UV curable polymer to the side walls of Pluronic channel leaving a defined culture space for endothelial cells.

2.1.1 Fabrication of PAAm-PDMS Composite Microwell Plate

A composite PAAm-PDMS microwell plate used for the generation and culture of tumor spheroids was fabricated by grafting polyacrylamide gel onto a preformed PDMS disk during the process of replica molding of the microwells. The microwell molds were 3D printed (Formlabs 3, USA) using standard resin to the dimensions disclosed herein. To fabricate monolithic PDMS disks with built-in gaskets, a plastic mold consisting of circular tapered groove (13 mm diameter, 0.5 μm tall, 1 mm wide) was 3D printed (Formlabs 3). The molds were spray-coated with ease-release 200 (Mann Release Technologies) to facilitate easy removal of the PDMS from 3D printed parts. Sylgard 184 PDMS (Dow Corning) was mixed in a volumetric 10:1 base to crosslinker ratio, degassed and poured onto the plastic mold. A flat polyethylene sheet was placed on top, and the setup was left to cure at 70° C. for 2 hours. Upon curing, the polyethylene sheet was then peeled away, and the PDMS disk was peeled from the plastic mold.

Polyacrylamide prepolymer with acrylamide to bisacrylamide (Bio-Rad) ratios of 7.5/0.24 wt % and 0.1% tetramethylethylenediamine (TEMED; Sigma-Aldrich, T7024) were prepared in a centrifuge tube. PDMS disks were treated with 10% w/v benzophenone (Acros Organics, NJ) in diluted acetone (65% in water) for 60 seconds, to swell and adsorb benzophenone into the silicone material. The samples were then rinsed with methanol and dried with nitrogen gas. 100 μL of freshly-prepared 1% w/v ammonium persulfate (APS) initiator was added to 900 μL of polyacrylamide prepolymer, mixed homogeneously using a vortex mixer and added to the microwell molds. The PDMS disks were placed on top of the molds concentrically and the setup was allowed to polymerize under UV light for 5 minutes to activate the surface-grafted benzophenone photoinitiator. Upon gelation, the PAAm layer with patterned microwell features grafted onto the PDMS disk was carefully peeled from the mold to form the PAAm-PDMS composite disk. The PDMS base was thereafter perforated by punching holes around the Polymerized PAAm using standard 1 mm biopsy punch. The PAAm-PDMS disks were washed three times with phosphate-buffered saline (PBS) and incubated in PBS overnight on a shaker, to leach out any excess unpolymerized toxins from the assembly. Prior to cell seeding, all the devices were kept hydrated by storing it under PBS at 4° C.

2.1.2 Sacrificial Bioprinting Enabled Fabrication of Porous Microchannels

Microfluidic channels were fabricated on a porous membrane by bioprinting a sacrificial channel layer which, upon creating a surrounding enclosure layer, was subsequently dissolved to leave behind open conduits that enable fluid flow over a permeable substrate. Commercially available Pluronic gel (IK50000, CellInk, USA) was used as the sacrificial layer, and an automated 3D Bioprinter (Bio X, CellInk, VA, USA) was used for printing this material to the desired contour of the microfluidic channel design pre-programmed into the bioprinter. After printing the pluronic layer, microfluidic tubes (EW-06419-01, Cole Parmer, USA) were stably positioned on the channel ends for creating the channel inlet and outlet. UV curable polymer NOA63 (Norland Inc., USA) was then cast on top of the pluronic gel, surrounding and enclosing the channel features. The setup was then exposed to 365 nm UV light for 5 min to completely polymerize and harden the NOA63 layer. The assembly was then cooled down to 4° C. for 15 mins after which the sacrificial pluronic gel was washed off by flushing the inlet and outlet tubes with cold PBS.

For TEER measurements, open microfluidic channels were fabricated. To accommodate the chopstick TEER probe inside the microchannel, the thickness of the sacrificial pluronic layer was increased and a precise volume of the UV curable glue was bioprinted surrounding the channel layer without creating any enclosure on top of the pluronic gel. Cold PBS added on top of the assembly dissolved the pluronic ink, creating an open conduit on top of the porous membrane.

B-2.2 Cell Culture

Breast tumor MDA-MB-231 were used as the representative tumor cell line, and Human Umbilical Vein Endothelial Cells (HUVECs) were used as the representative endothelial model. HUVECs were cultured in endothelial growth media (ScienCell, 1001) supplemented 5% Fetal Bovine Serum (FBS), 1% Penicillin-Streptomycin (Pen-Strep, Gibco, USA) and 1% Endothelial cell growth supplement (ScienCell, 1052). MDA-MB-231 were cultured in high glucose Dulbecco's Modified Eagle Medium (DMEM) supplemented with 10% FBS, 1% Pen-Strep. Cells were cultured in standard cell culture flasks at 37° C. in a humidified incubator with 5% $CO_2$ atmosphere. Immediately prior to the experiments, the cells were detached from the culture plates using Trypsin-EDTA (0.25%), and re-suspended in complete growth medium to the desired concentration.

2.2.1 Microfluidic Endothelial Culture

Prior to endothelial cell seed, all fabricated microchannel were exposed to germicidal UV light for 30 min and washed twice with PBS to remove any residual Pluronic. Then the microfluidic channel was surface coated with Poly-I-lysine or collagen and stored overnight at 4° C. The channel was washed twice with PBS to remove excess Poly-I-lysine or Collagen. Afterwards, HUVECs was seeded to the microchannel with seeding density of $5\times10^6$ $ml^{-1}$. Excess HUVECs were removed after 2 hours of post-seeding. The seeded microfluidic channel integrated insert placed in multiwell dish with culture media incubated at 37° C. and 5% $CO_2$.

2.2.2 Generation of Tumoroids

To generate tumor spheroids, the PAAm-PDMS disks were sterilized by exposure to UV light for 30 min; thereafter 100 μL of the tumor cell suspension (at a concentration of $5\times10^{6}$ $ml^{-1}$) under sterile conditions was gently pipetted onto the PAAm surface. The setup was left undisturbed for 5 min to allow the cells to settle into the microwells by gravity. Thereafter, the PAAm microwells were gently rinsed with culture media to wash off the excess cells on the surface of the microwell plate. The fabricated devices step up were stored inside multiwell plates with culture media and incubated at 37° C. and 5% $CO_2$ for 24 hours to allow for the initial spheroid compaction.

B-2.3. Immunostaining

To assess the intracellular adheres junctions of endothelial cells cultured on fabricated microfluidic channel, endothelial cells were labeled with vascular endothelial cadherin (VE-cadherin) and nuclei in culture, using standard indirect immunostaining techniques. Endothelial cells were initially washed in PBS and fixed in 4% (v/v) paraformaldehyde in PBS for 1 h at room temperature. Thereafter the devices were washed twice with PBS for 5 min each and permeabilized with 0.1% (v/v) Triton-X in PBS for 10 mins at room temperature. After washing 2 times with PBS for 5 min each again, the endothelial cells were blocked against non-specific binding with 2.5% (v/v) goat serum in PBS for 1 h at room temperature. Then cells were then incubated overnight at 4° C. with rabbit anti-VE cadherin monoclonal antibody (Invitrogen) in a 1:500 dilution of goat serum. Cells were washed and incubated with the 2.5% (v/v) goat serum for 30 minutes, before incubation in a 1:500 dilution of goat anti-rabbit IgG (Abcam ab150116) secondary antibody tagged with Texas red and diluted in 2.5% goat serum, for 1 hour at room temperature. Samples were then thoroughly washed in PBS, and cell nuclei were stained using a 2 μg/ml DAPI (Invitrogen) in PBS for 30 minutes.

B-2.4 Trans-Endothelial Electrical Resistance (TEER) Measurements

Electrical resistance across HUVECs was measured using the electrical cells sensor system, the Volt-ohm meter (Millicell-ERS, Millipore, World Precisions, Saratoga, FL, USA). TEER values were obtained for each day after the endothelial monolayer formation (day 1-6) and upon co-culture with tumor cells (24, 48, 72 hours: day 7-9). For TEER assay, the Volt-Ohm meter was calibrated each time before use and the electrodes were sterilized in 70% ethanol for 10 min and air-dried. The electrode containing the shorter arm was placed in the upper compartment and longer arm was placed in the lower well of the Transwell® with enough media until constant measurement values were obtained. The Transwell® polycarbonate membrane insert without cells was used as the blank while the other wells containing cells served as treatment samples (n=3).

B-3. Results 3.1 Vascularization of the Microfluidic Channel

For analysis of any multicellular culture model, it is important to maintain segregated cultures of the involved cell types till attaining their phenotypic maturation, before introducing them into a co-culture. The first characterization was of the endothelial culture in the porous microfluidic channel and the advantage of magnetic attachment for hybrid integrating the co-culture setup on-demand, was leveraged to characterize changes in the endothelial behavior upon co-culture with tumoroids.

To circumvent the uncertainties of live-tracking the growth and spread of cells cultured on track-etched porous membranes, we characterized the HUVEC culture inside the porous microchannels by monitoring the formation of endothelial tight junction barrier via routine TEER measurements during the culture time-course, complemented by end-point immunostaining for the junction marker VE-Cadherin at every 24 hours of culture. The open channel configuration of a device of the present application facilitated the use of the standard chopstick probes for TEER measurement. Expected spread and growth behavior of the HUVECs was observed in the channels developed on the porous membrane using the sacrificial bioprinting method, including the formation of tight junctions within 3 days of culture. The formation of a confluent HUVEC monolayer within sections of serpentine microfluidic channels that contain sharp corners and curvatures was confirmed. The TEER values increased with the culture duration; Absolute TEER values can vary depending upon biophysical factors such as the cell type, cell seeding density, culture substrate or the passage number, but they reach peak value when the endothelium forms a tight barrier. The TEER values were observed to peak on day 7. The results from the immunostaining also showed a significantly increased expression of VE-Cadherin marker after 7 days of culture compared to a 1 day culture, consistent with the increase in TEER corresponding to the formation of endothelial tight junctions. However, no significant difference was observed in the tight junction length per unit area even after 72 hours of peak TEER value, suggesting the sustenance of functionally tight cell-cell junctions after day 7 of the HUVEC culture within the channel.

Magnetically hybrid integrated the tumor-microwell plates with mature HUVECs cultured over 7 days, mimicked an intact early-stage tumor-vasculature. The magnetic attachment method of the present application enabled easy alignment of the tumoroids with respect to the microfluidic channel. The design, fabrication and the integration process facilitated use of a wide variety of tumor-vasculature configurations, enabling different arrangements of the tumoroids with respect to the channel contour and for defining relative spatial localization along all three axes.

To study the effect of the tumor location on the endothelial regulation, the experimental system had a microfluidic channel and a single array of tumoroids, where the width of the channel was at least 10-times the diameter of the tumoroids. Since the endothelial proliferation rate has a greater effect on the spread and extent of vascular growth than the migration rate, the HUVECs were immunostained for Ki67 and the 24 h proliferation behavior at different regions of the micro-channel relative to the location of a tumoroid were observed. When imaging the HUVECS located within the field of view of the tumoroids, the tumor microwell plate was reversibly detached from the assembly. Almost ~30% of the HUVECs in proximity (less than 350 μm) to the tumoroids showed Ki67 signal, and this fraction gradually decreased with increasing distance between the HUVECs and the tumoroids. HUVECs located within 350 μm showed a significantly greater proliferation ($p<0.05$) than the cells present within the range of 350 ~ 700 μm. However, no significant proliferation difference was observed for HUVECs located farther than 700 μm from the tumoroids, and a control monoculture. Design of in-vitro platforms for tumor-endothelial co-culture studies should take into consideration the interactional proximity of individual cell types.

B-3.2 Modeling Tumor-Mediated Developmental Angiogenesis

During the initial stages of angiogenesis, tumor cells induce structural disturbances in a nearby blood vessel by affecting its endothelial cell-cell adherence junctions. The 24-hr tumor-endothelial co-culture assay did not show typical angiogenesis-like behavior, such as directional endothelial cell migration or tube formation; it is likely that endothelial angiogenesis is dependent upon the duration of tumor interactions within the co-culture model.

3.2.1 Tumor-induced degradation of Endothelium

Tumoroids may disrupt the endothelium and promote intercellular gaps between the endothelial cells by initiating both endothelial cell adherens junction disassembly and contractility. To test this, tumor-induced degradation of the tight junctions between endothelial cells was measured every 24 hours of co-culture. Within the first 24 hours of tumor-endothelial hybrid integration, a loss of VE-cadherin corresponded with a significant drop in the TEER values and an increased endothelial cell count, compared to the respective monoculture controls at the same time point. A significant decrease in the nucleus area of the HUVECs in the co-culture suggests they adopted a more compacted cell and nuclear morphologies in the presence of tumors. These data suggest that the inter-cellular biochemical signaling within the tumor-vascular microenviroenment causes vascular disruption could lead to angiogenesis.

3.2.2 Endothelial YAP/TAZ Nuclear Localization

To ascertain the developmental angiogenesis-like tumor-endothelial dynamics modeled by the M-TVOT device, the role of endothelial YAP/TAZ activation was studied. VE-Cadherin is present along the adherent junctions are connected to the actin cytoskeleton through phosphorylated YAP/TAZ. Loss of VE Cadherin along the endothelial junctions, when angiogenesis-mediated could result in the YAP/TAZ nuclear translocation; the HUVECs were stained for YAP/TAZ to quantify their intra-cellular distribution. A substantial population of the HUVECs showed YAP/TAZ nuclear localization with 24 h tumor co-cultures, with the co-localization of YAP and TAZ observed under all conditions. As quantified and corroborated through integrated fluorescence density measurements that showed a significantly greater ($p<0.05$) nuclear presence of the endothelial YAP/TAZ in tumor co-cultures.

The presence of tumoroids promotes junctional VE-cadherin disruption of the endothelium that in-turn regulates YAP/TAZ nuclear translocation. Tumor-driven nuclear localization of the YAP/TAZ may regulates certain transcription factors.

Tumor-stimulated proliferative, and permeable vasculature assume a pro-angiogenic organization prior to branching out, and the M-TVOT device disclosed herein can model the in-vivo behavior of the tumor-vascular interactional dynamics in a time-dependent manner.

B-3.3 Demonstration of Anti-Angiogenic Drug Testing

VEGF-supplemented media (40 ng/ml) was inserted into the VEGF injection channels and the control mediums without VEGF were used as reference. The HUVECs were monitored daily for 5 days by phase-contrast microscopy. On day 5, the HUVECs were fixed and stained to examine cell morphologies. Cells actively migrated from the endothelial channel into the collagen matrix (condition-side) toward the spheroids. No migration was observed into the collagen across the porous membrane without the tumoroids, thereby suggesting the migratory response of the HUVECs.

Expression was at higher levels in the absence of bortezomib (0 μM, average=18.2%) and its expression ratio gradually decreased with increasing bortezomib concentration at day 1 (from 18.2% at 0 μM to 7.8% at 1 μM), but declined more by day 2 (from 18.2% at 0 μM to 3.6% at 1 μM). The Ki67 expression ranged from 18.5% at 0 nM to 6.70% at 10 nM on day 1 and 18.34% at 0 nM to 4.24% at 10 nM on day 2. The proliferation rate varies in a time and dose dependent manner; Ki67 was expressed in less than 5% of the HUVECs.

Confocal microscopy revealed the growth of circular lumen-like structures from the HUVEC monolayer into the condition-side hydrogel scaffolds in response to VEGF. No morphological change was evident in the control-side hydrogel scaffolds in immunostained and confocal microscopy images, but several cells had migrated. These cells were not connected to the endothelial monolayer by vascular stalks presumably due to the absence of a VEGF concentration gradient across the collagen gel. The number of cells that migrated from each opening into collagen gel scaffolds were counted: 79+9.8 cells migrated and proliferated toward the condition-side hydrogel scaffolds and 8+2.3 cells migrated toward the control-side hydrogel scaffolds.

Tumor-secreted Vascular Endothelial Growth Factor (VEGF) functions as a potent stimulant of the pro-angiogenic endothelial switch. VEGF Receptor signaling during angiogenesis stimulates YAP/TAZ through cytoskeletal remodeling and in turn, actived endothelial YAP/TAZ induce a downstream transcriptional program which regulates proliferation, actin cytoskeleton contractility, cell adhesion, leading to collective cell migration. In the device of the present application, the VEGF secreted by the tumoroids mediated the angiogenesis-like endothelial regulation. The efficacy of VEGF-targeting anti-angiogenic drug Bevacizumab (Avastin) was measured using a treatment condition that did not result in significant toxicity for HUVECs or the tumor cells, but inhibited the pro-angiogenic switch.

After hybrid integration of the HUVECs and the tumoroid cultures, Bevacizumab was perfused into the microfluidic channel at a concentration prescribed by its IC50 value. In comparison with the untreated co-culture, 24 h treatment with Avastin significantly preserved the endothelial integrity as measured by TEER, VE-Cadherin immunostaining for tight junction length and endothelial YAP/TAZ nuclear localization, supporting the active role of tumor-secreted VEGF mediated endothelial disruption leading to angiogenesis.

In a typical tumor vasculature in-vivo, systemic delivery of drugs to the tumor sites is affected through diffusion across the vascular linings into the tumor tissue. Using the device model of the present application, 50 μM Avastin was injected into the microfluidic channel and the integrity of the endothelial monolayer was evaluated.

It will be understood that various details of the presently disclosed subject matter may be changed without departing from the scope of the presently disclosed subject matter. Furthermore, the foregoing description is for the purpose of illustration only, and not for the purpose of limitation.

The invention claimed is:

1. A heterogeneous co-culture system, wherein said system comprises a pair of inert, axially magnetized rings held at a fixed distance apart, wherein the fixed distance is less than 0.5 mm; and wherein the heterogeneous co-culture system:

accommodates cell cultures growing in 2 dimensions and cell cultures growing in 3 dimensions;

provides spatial compartmentalization and controllable positioning of 2D cell cultures and 3D tissue and tumor cultures; and integrates the cell cultures growing in 2 dimensions and the cell cultures growing in 3 dimensions in a reversibly attachable manner.

2. The heterogeneous co-culture system of claim 1, wherein the cell cultures are prepared by tissue engineering, using synthetic or clinical tissue samples.

3. The heterogeneous co-culture system of claim 1, wherein the cell cultures growing in 3 dimensions are spheroids.

4. The heterogeneous co-culture system of claim 1, wherein the fixed distance is maintained by an O-ring or washer.

5. The heterogeneous co-culture system of claim 1, wherein the fixed distance is between 0.1 mm and 0.5 mm.

6. The heterogenous co-culture system of claim 1, further comprising a cell culture platform selected from the group comprising petri dish, multiwell plates, or slides.

7. The heterogenous co-culture system of claim 6, further comprising a first insert comprising a porous substrate, wherein the porous substrate optionally comprises plastic, hydrogel, or biological tissues.

8. The heterogenous co-culture system of claim 7, further comprising a second insert comprising a porous substrate, wherein the porous substrate optionally comprises plastic, hydrogel, or biological tissues.

9. The heterogenous co-culture system of claim 7, wherein the first insert is optically transparent.

10. The heterogenous co-culture system of claim 6, wherein the cell culture platform is optically transparent.

11. The heterogenous co-culture system of claim 1, wherein cell cultures growing in 2 dimensions and cell cultures growing in 3 dimensions are grown independently, optionally to attain fully mature phenotypes, before being integrated into the co-culture system.

12. The heterogenous co-culture system of claim 1, further comprising a cell culture platform comprising a microfluidic system.

13. The heterogenous co-culture system of claim 12, wherein a plurality of cells are co-culture along their apical-basil axis within the microfluidic system.

14. A heterogeneous co-culture system, wherein said system comprises a pair of inert, axially magnetized rings positioned at a fixed distance between 0.1 mm and 0.5 mm; and wherein the heterogeneous co-culture system is configured to:

accommodate a plurality of cell cultures growing in at least two dimensions;

provide spatial compartmentalization and controllable positioning of two-dimensional cell cultures and three-dimensional tissue and tumor cultures; and integrate the plurality of cell cultures growing in the at least two dimensions in a reversibly attachable manner.

15. The heterogenous-culture system of claim 14, wherein the heterogeneous co-culture system is configured to independently accommodate cell cultures growing in 2 dimensions and cell cultures growing in 3 dimensions.

16. The heterogenous-culture system of claim 14, further comprising a first insert and a second insert.

17. The heterogenous-culture system of claim 14, further comprising a cell culture platform comprising a microfluidic system.

18. A method, the method comprising:

accommodating a plurality of two dimensional cell cultures and a plurality of three dimensional tissue and tumor cultures within a heterogeneous co-culture platform comprising a pair of inert, axially magnetized rings held at a fixed distance apart, wherein the fixed distance is less than 0.5 mm;

providing spatial compartmentalization and controllable positioning of the plurality of two dimensional cell cultures and the plurality of three dimensional tissue and tumor cultures within the heterogeneous co-culture platform; and integrating the plurality of two dimensional cell cultures and the plurality of three dimensional tissue and tumor cultures within the heterogeneous co-culture platform in a reversibly attachable manner.

19. The method of claim 18, wherein the fixed distance is between 0.1 mm and 0.5 mm.

20. The method of claim 18, comprising independently growing the plurality of two dimensional cell cultures and the plurality of three dimensional tissue and tumor cultures to attain fully mature phenotypes, prior to integration into the co-culture system.

* * * * *